(12) United States Patent
Adams

(10) Patent No.: US 6,342,060 B1
(45) Date of Patent: Jan. 29, 2002

(54) TENDON PASSING DEVICE AND METHOD

(76) Inventor: Brian D. Adams, 3673 Forest Gate Dr., NE., Iowa City, IA (US) 52240

( * ) Notice: Subject to any disclaimer, the term of this patent is extended or adjusted under 35 U.S.C. 154(b) by 0 days.

(21) Appl. No.: 09/378,075

(22) Filed: Aug. 20, 1999

Related U.S. Application Data

(60) Provisional application No. 60/111,490, filed on Dec. 8, 1998.

(51) Int. Cl.[7] .............................................. A61B 17/04
(52) U.S. Cl. ..................... 606/151; 606/232; 623/13.15
(58) Field of Search ................................ 606/152, 151, 606/150, 153, 232, 70–72; 285/235, 38; 623/13.15, 13.11

(56) References Cited

U.S. PATENT DOCUMENTS

| | | | |
|---|---|---|---|
| 3,176,316 A | * | 4/1965 | Bodell ................................. 3/1 |
| 3,545,008 A | * | 12/1970 | Bader, Jr. ........................... 3/1 |
| 3,633,582 A | | 1/1972 | Steinman ..................... 128/334 |

(List continued on next page.)

FOREIGN PATENT DOCUMENTS

| | | | |
|---|---|---|---|
| EP | 0 820 725 A2 | 1/1998 | ............ A61B/17/11 |
| WO | WO 96/16612 | 6/1996 | ............. A61F/2/08 |
| WO | 97/37002 | 10/1997 | ............ C12N/5/06 |

OTHER PUBLICATIONS

International Search Report for PCT/US 99/11821 mailed Sep. 6, 1999.
"The Pactan Repair Device," *Small Joint Orthopaedic*, by Wright Medical Technology, Inc.
"Plastic & Reconstructive/Hand Surgery" by Accurate Surgical & Scientific Instruments Corp.
"Goldstein Microspike, Approximator Clamps fr Vasovasostomy & Vasoepididymostomy," *Accurate Surgical& Scientific Instruments Corporation*.
"Surgery of Peripheral Nerves and Tendons" by V.E. Meyer, *S&T Marketing Ltd.*
"Flexor Tendon Injuries: I. Foundations of Treatment" by James W. Strickland, M.D., *Journal of the American Academy of Orthopaedic Surgeons*, vol. 3, #1, Jan./Feb. 1995.
"Flexor Tendon Injuries: II. Operative Technique" by James W. Strickland, M.D., *Journal of the American Academy of Orthopaedic Surgeons*, vol. 3, #1, Jan./Feb. 1995.
International Search Report for PCT/US 99/23491, Feb. 1, 2000.

*Primary Examiner*—David O. Reip
*Assistant Examiner*—Julian W. Woo
(74) *Attorney, Agent, or Firm*—Baker Botts L.L.P.

(57) ABSTRACT

Apparatus and methods are provided to facilitate passage of lacerated ends of a tendon back into and/or through an associated sheath. The method is often necessary to complete repair when lacerated ends of a tendon retract from the associated laceration site in the sheath. The method includes applying respective elastomeric tubes over lacerated ends of the tendon. Each elastomeric tube is preferably made of thin, elastic rubber. The elastomeric tube also prevents fraying and catching of the respective lacerated end during passage into and through the sheath. Multiple threads are preferably engaged with the elastomeric tube. An applicator is provided to slide a respective elastomeric tube over each lacerated end of the tendon. Each elastomeric tube is placed over the respective lacerated end of the tendon by pulling on the associated threads. After the tube is applied, the applicator is removed. The threads, along with suture strands previously placed in the tendon end, are then used to pull the tube and lacerated end into and through the sheath. Once the tendon is passed through its sheath, the tube is removed by pulling it off the end of the tendon using the threads. A second tube may be applied to the other lacerated end of tendon if necessary. The applicator and elastomeric tube or tubes are preferably discarded at the completion of the surgical repair procedure.

4 Claims, 7 Drawing Sheets

U.S. PATENT DOCUMENTS

| | | | |
|---|---|---|---|
| 3,745,590 A | * 7/1973 | Stubstad | 3/1 |
| 4,469,101 A | 9/1984 | Coleman et al. | 128/334 R |
| 4,553,543 A | 11/1985 | Amarasinghe | 128/334 R |
| 4,585,458 A | 4/1986 | Kurland | 623/13 |
| 4,602,634 A | 7/1986 | Barkley | 128/334 |
| 4,635,636 A | 1/1987 | Goldstein | 128/334 |
| 4,641,860 A | * 2/1987 | McMickle et al. | 285/38 |
| 4,723,548 A | 2/1988 | Lalonde | 128/335 |
| 4,960,420 A | 10/1990 | Goble et al. | 606/72 |
| 5,007,920 A | 4/1991 | Torre | 606/207 |
| 5,251,642 A | 10/1993 | Handlos | 128/774 |
| 5,298,012 A | 3/1994 | Handlos | 600/36 |
| 5,366,457 A | 11/1994 | McGuire et al. | 606/86 |
| 5,415,651 A | 5/1995 | Schmieding | 606/1 |
| 5,464,415 A | 11/1995 | Chen | 606/153 |
| 5,534,008 A | 7/1996 | Acksel | 606/148 |
| 5,593,024 A | * 1/1997 | Seiler | 206/5 |
| 5,624,453 A | 4/1997 | Ahmed | 606/140 |
| 5,649,937 A | 7/1997 | Bito et al. | 606/139 |
| 5,656,605 A | 8/1997 | Hansson et al. | 514/21 |
| 5,697,933 A | 12/1997 | Gundlapalli et al. | 606/96 |
| 5,746,757 A | 5/1998 | McGuire | 606/148 |
| 5,800,544 A | 9/1998 | Demopulos et al. | 623/13 |
| 5,843,098 A | 12/1998 | Allen et al. | 606/144 |
| 5,964,764 A | * 10/1999 | West, Jr. et al. | 606/72 |

* cited by examiner

TENDON PASSING DEVICE AND METHOD

RELATED PATENT APPLICATIONS

This application claims the benefit of U.S. Provisional Application Ser. No. 60/111,490, filed Dec. 8, 1998, entitled Tendon Passing Device and Method.

This patent application is related to pending U.S. patent application U.S. Ser. No. 09/286,198 filed Apr. 5, 1999, entitled Apparatus and Method for Placing Sutures in the Lacerated End of a Tendon and Similar Body Tissues and U.S. provisional application Ser. No. 60/088,153 filed Jun. 5, 1998 entitled Tendon Suture-Repair Device and Method.

TECHNICAL FIELD OF THE INVENTION

The present invention relates generally to medical devices and more particularly to a passing device for use in performing tenorrhaphy and similar surgical procedures.

BACKGROUND OF THE INVENTION

A wide variety of procedures and equipment are used to perform tenorrhaphy, the union of a divided or ruptured tendon by suturing or tenodesis, the suturing of the end of a tendon to a bone. Tendon repair is difficult to satisfactorily perform, especially in the digits, due to the size and other characteristics of tendons, their associated tendon sheath and correspondingly small surgical field.

During tendon repair, it is important to minimize any further damage to a lacerated tendon and its associated sheath. Often, the lacerated ends of a tendon are not available at the laceration site in the associated sheath. Even if lacerated ends of a tendon can be grasped through the laceration site in the associated sheath, it may not be possible to deliver a sufficient length of tendon from the laceration site to accomplish a suture repair. Thus, additional openings are often surgically created proximal and distal to the laceration site in the associated sheath to allow extracting lacerated ends of the tendon from the sheath. Sutures may then be respectively placed in the lacerated ends of the tendon. The tendon ends and sutures must then be passed back into the sheath through the respective surgical openings to allow completion of the tendon repair within the associated sheath. Lacerated tendon ends tend to fray when handled, especially when an attempt is made to pass the tendon ends through tight openings in the associated sheath.

SUMMARY OF THE INVENTION

Accordingly, a need has arisen for improved equipment and methods to protect the ends of lacerated tendons, ligaments and other types of fibrous body tissue. One aspect of the present invention includes an elastomeric tube and an applicator for placing the elastomeric tube over the lacerated end of a tendon, ligament and other fibrous body tissues.

Technical benefits of the present invention include tendon repair procedures and equipment satisfactory for use with contemporary surgical practices and rehabilitation programs. Tendon passing devices and associated tendon repair procedures incorporating teachings of the present invention substantially reduce or eliminate further damage to a tendon and its associated sheath during tenorrhaphy. Such tendon passing devices and associated tendon repair procedures substantially reduce or eliminate fraying of the ends of a ruptured or lacerated tendon during tenorrhaphy and/or when passing a tendon graft through a bone tunnel.

Another aspect of the present invention includes providing apparatus and methods which may be used to repair lacerated tendons or ligaments in a patient's upper and lower extremities. Apparatus and methods incorporating teachings of the present invention may also be used to pass tendons, tendon grafts or fibrous body tissues through bone tunnels during reconstructive surgery such as to repair ligament injury or damage from arthritis and other diseases. Apparatus and methods incorporating teachings of the present invention may also be used during tendon transfers associated with treatment of palsies and reconstruction of congenital deformities.

Further technical benefits of the present invention include protecting the lacerated ends of a tendon or other types of fibrous body tissue during a surgical procedure. For some procedures such as tenorrhaphy, surgical openings may be formed in the sheath of a lacerated tendon at optimum locations proximal and distal to the laceration site to allow extracting respective lacerated ends of the tendon from the sheath. Sutures may be placed in each lacerated end of the tendon for use in repairing the tendon. Each tendon end is preferably covered with a respective elastomeric tube to provide protection from fraying or other damage while passing the lacerated end of the tendon and associated suture strands through the respective surgical opening. The elastomeric tubes and suture strands cooperate with each other to aid in positioning the lacerated ends of the tendon at the optimum position within the associated sheath for completion of the tendon repair.

BRIEF DESCRIPTION OF THE DRAWINGS

For a more complete understanding of the present invention, and advantages thereof, reference is now made to the following brief descriptions, taken in conjunction with the accompanying drawings and detailed description, wherein like reference numerals represent like parts, in which.

DETAILED DESCRIPTION OF THE INVENTION

Figure 1:
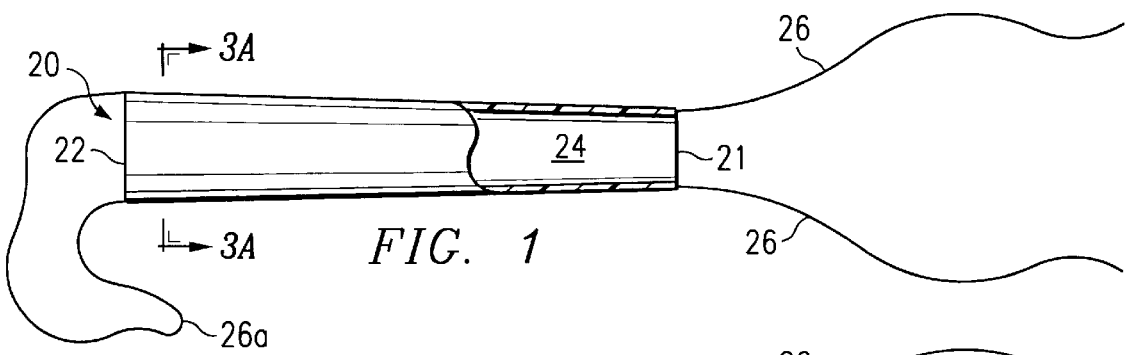
FIG. 1 is an enlarged schematic drawing in elevation and in section with portions broken away showing an elastomeric tube which may be placed over the lacerated end of a tendon, ligament and other types of fibrous body tissue in accordance with teachings of the present invention.

Preferred embodiments of the present invention and its advantages are best understood by referring now in more detail to FIGS. 1–26 of the drawings, in which like numerals refer to like parts.

Apparatus and methods incorporating teachings of the present invention may be satisfactorily used to repair lacerated tendons or ligaments in a patient's upper and lower extremities and suturing the end of a tendon or ligament to a bone. Apparatus and methods incorporating teachings of the present invention may also be satisfactorily used to pass tissue grafts through bone tunnels during reconstructive surgery such as to repair ligament injury or joint damage from trauma or degenerative diseases such as arthritis. Apparatus and methods incorporating teachings of the present invention may be satisfactorily used to repair various types of relatively small fibrous body tissues such as tendons and ligaments.

Tendons may be generally described as fibrous cords (not expressly shown) or bands of body tissue which connect associated muscles to a bone. Ligaments may be described as fibrous cords (not expressly shown) or bands of body tissue which connect bones or cartilages with each other to support and strengthen an associated joint. Tendons and ligaments are generally composed of multiple collagen bundles and as a result have some of the characteristics associated with a braided rope. When a tendon or ligament is lacerated, the resulting ends have a tendency to fray during manipulation while performing surgical repairs.

The term "lacerated" is used to describe a tendon, ligament and similar types of fibrous body tissue which has been cut, torn, ripped or ruptured.

Various embodiments of the present invention shown in FIGS. 1 through 5 include elastomeric tubes 20, 20a and 20b and applicator 30. Suture thread snare 90 shown in FIG. 6 may be used in performing tenorrhaphy and similar surgical procedures in accordance with teachings of the present invention. For purposes of explanation, elastomeric tubes 20, 20a and 20b and applicator 30 will be described with respect to repairing a lacerated tendon and particularly repairing a typical flexor tendon disposed within a sheath adjacent to one of the bones in a patient's finger or digit.

Elastomeric tubes 20, 20a and 20b may be formed from thin, latex type rubber or other suitable elastomeric materials. Elastomeric tubes 20, 20a and 20b are preferably formed from selected materials which are biocompatible with tendons, ligaments and other types of body tissue for at least several hours. Materials used to form elastomeric tubes 20, 20a and 20b preferably have sufficient resiliency or elasticity to allow portions of each tube having at rest dimensions of approximately two to four millimeters to be expanded to approximately twelve to fourteen millimeters. The selected elastomeric materials preferably have sufficient flexibility to allow rolling elastomeric tubes 20, 20a and 20b into generally oval shaped ring or toroid 28 or to allow sliding elastomeric tubes 20, 20a and 20b onto and off of applicator 130. See FIGS. 4A, 4B, 8 and 9. For some applications various types of biocompatible lubricants may be placed on the exterior and/or interior of elastomeric tubes 20, 20a and 20b.

Figure 2:
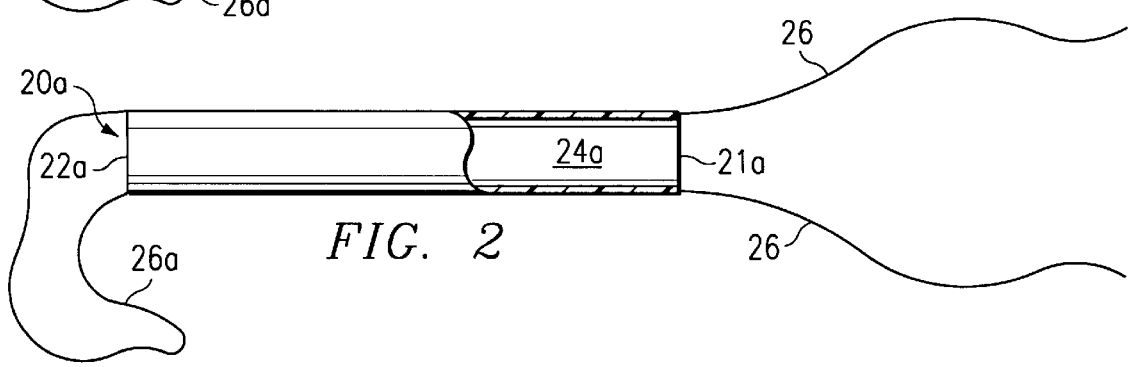
FIG. 2 is an enlarged schematic drawing in elevation and in section with portions broken away showing another embodiment of an elastomeric tube which may be placed over the lacerated end of a tendon, ligament and other types of fibrous body tissue in accordance with teachings of the present invention.

Elastomeric tube 20, as shown in FIG. 1, is substantially the same as elastomeric tube 20a shown in FIG. 2 except elastomeric tube 20 has a tapered exterior surface and a tapered cross section extending from first end 21 to second end 22. Elastomeric tube 20a has a general uniform exterior surface and a general uniform cross section extending from first end 21a to second end 22a. First end 21 of elastomeric tube 20 and first end 21a of elastomeric tube 20a may sometimes be referred to as the "leading end."

Figure 3A:
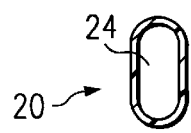
FIG. 3A is an enlarged schematic drawing in section taken along lines 3A—3A of FIG. 1.
Figure 3B:
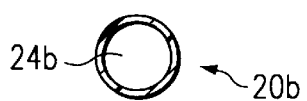
FIG. 3B is an enlarged schematic drawing showing a cross section of an elastomeric tube incorporating a further embodiment of the present invention.

For some applications elastomeric tubes 20 and 20a may have generally oval shaped cross sections such as shown in FIG. 3A. For other applications elastomeric tubes 20 and 20a may have generally circular cross sections similar to elastomeric tube 20b as shown in FIG. 3B. Elastomeric tube 20b and its generally circular cross section will be discussed later in more detail.

Flexor tendons have a generally oval shaped cross section varying in size for adults from approximately five millimeters by two millimeters to eight millimeters by three millimeters. An average flexor tendon for an adult has an oval shaped cross section of approximately six millimeters by two millimeters. The dimensions and configuration of elastomeric tubes 20, 20a and 20b are preferably selected to accommodate passing or inserting the lacerated end of a flexor tendon into its associated sheath. For some applications elastomeric tubes 20, 20a and 20b may have a length of approximately fifteen millimeters (15 mm).

For the embodiment of the present invention as shown in FIG. 1, first end 21 of elastomeric tube 20 may have an opening smaller than the opening at second end 22 with longitudinal passageway 24 extending there between. In its at rest or unexpanded state as shown in FIG. 1, first end 21 may have a generally oval configuration with dimensions of approximately two millimeters by one millimeter. Second end 22 may have a similar oval configuration with dimensions of approximately four millimeters by one millimeter. First end 21a and second end 22a of elastomeric tube 20a may have generally oval shaped configurations with substantially the same dimensions of approximately three millimeters by one millimeter. FIG. 3A shows a typical oval shaped cross section which may be associated with elastomeric tubes 20 and 20a.

For other applications elastomeric tubes 20 and 20a may have a generally circular cross section similar to elastomeric tube 20b as shown in FIG. 3B. For such embodiments of the present invention (not expressly shown), elastomeric tube 20 would have a generally circular configuration at first end 21 with a diameter of approximately one and a half millimeters and a generally circular configuration at second end 22 with a diameter of approximately three millimeters.

The diameter of the cross section of elastomeric tube 20b may be uniform and approximately two or three millimeters. An elastomeric tube having a generally uniform circular cross section extending throughout the length thereof may be more cost effective to manufacture as compared to an elastomeric tube having an oval shaped cross section and/or a tapered cross section extending between the associated first end and second end. For some applications, elastomeric tube 20b having a generally circular cross section may be preferred for use in repairing tendons, ligaments and other types of fibrous body tissues in accordance with teachings of the present invention.

Elastomeric tubes having cross sections other than oval or circular may be satisfactorily placed on the lacerated end of a tendon, ligament or other types of fibrous body tissue in accordance with teachings of the present invention. The present invention is not limited to elastomeric tubes having cross sections such as shown in FIGS. 3A and 3B.

A plurality of threads 26 are preferably engaged with tube 20 and extend longitudinally from first end 21. Respective threads 26 may also be engaged with tube 20a extending longitudinally from first end 21a and with elastomeric tube 20b. Various types of biocompatible adhesives may be satisfactorily used to attach threads 26 to the exterior of respective elastomeric tubes 20, 20a, and 20b. For some applications threads 26 may be embedded, during the manufacturing process, within the wall of respective elastomeric tubes 20, 20a, and 20b. A variety of techniques may be satisfactorily used to engage threads 26 with elastomeric tubes 20, 20a and 20b.

Threads 26 may be used to unroll elastomeric tube 20, 20a, and 20b from applicator 30 over a lacerated end of a tendon or ligament or to slide elastomeric tubes 20, 20a and 20b from applicator 130 over a lacerated end of a tendon or ligament. Threads 26 may also be used to guide or pass the lacerated end of a tendon or ligament enclosed within elastomeric tube 20, elastomeric tube 20a, or elastomeric tube 20b into and through an associated tendon sheath (see FIGS. 16–21) or through a bone tunnel (see FIGS. 23–26). Threads 26 preferably minimize or prevent any undesired longitudinal stretching or undesired movement of the associated elastomeric tube without restricting radial expansion or contraction.

For some applications, threads 26 preferably extend from second end 22 of elastomeric tube 20 and second end 22a of elastomeric tube 20a to form respective loops 26a. During manipulation of the lacerated end of a tendon or ligament, which will be discussed later in more detail, each loop 26a cooperates with other portions of the associated thread 26 to maintain the respective elastomeric tube 20, 20a or 20b satisfactory disposed on the lacerated end of the tendon or ligament. Loop 26a is preferably provided to prevent undesired movement of the associated elastomeric tube relative to the end of a lacerated tendon, ligament or other types of fibrous body tissue.

Figure 4A:
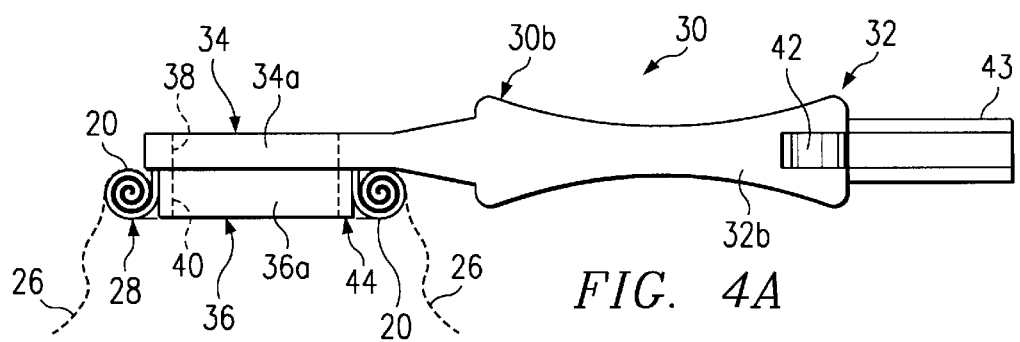
FIG. 4A is a schematic drawing in elevation with portions broken away showing a side view of an applicator in its first, closed position with an elastomeric tube mounted thereon for placement on the lacerated end of a tendon, ligament and other types of fibrous body tissue in accordance with teachings of the present invention.
Figure 4B:
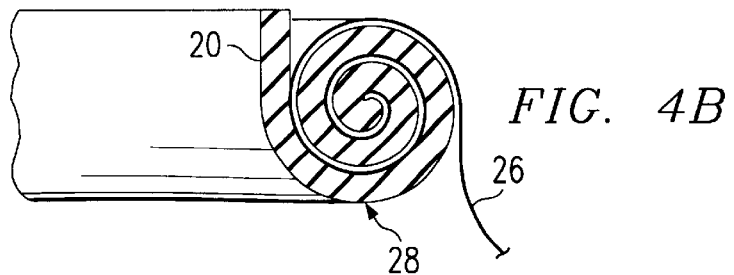
FIG. 4B is an enlarged schematic drawing in section showing portions of an oval ring or toroid formed by rolling the elastomeric tube of FIG. 1.
Figure 5:
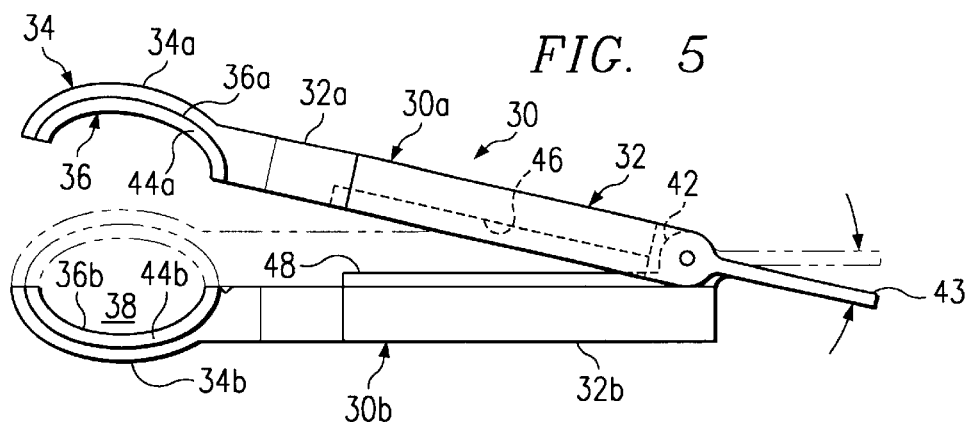
FIG. 5 is a schematic drawing showing a plan view of the applicator of FIG. 4A in its second, open position.

For the embodiment of the present invention as shown in FIGS. 4A, 4B, and 5, applicator 30 is preferably sized for relatively easy manipulation during a surgical procedure such as tenorrhaphy. Applicator 30 may be formed from various types of polymeric and copolymeric materials such as acrylic resin, polypropylene or other suitable materials to allow disposal after completion of the surgical procedure. For other applications, applicator 30 may be formed from various metal alloys, cements and/or composite materials.

Applicator 30 may have an overall length of approximately four to five centimeters (4–5 cm). The dimensions and configuration of handle 32 are preferably selected to allow holding applicator 30 between a surgeon's index finger and thumb. Various features of applicator 30 will be described with respect to placing an elastomeric tube such as elastomeric tubes 20, 20a or 20b on the lacerated end of a tendon. However, applicator 30 may be used to place a wide variety of elastomeric tubes formed in accordance with teachings of the present invention on the lacerated end of a tendon, ligament or other types of fibrous body tissue. For one application applicator 30 holds an elastomeric tube formed in accordance with teachings of the present invention in a stretched and rolled-up state so that applicator 30 and the respective elastomeric tube may be placed over a lacerated end of a tendon at an appropriate location for unrolling the elastomeric tube onto and over the lacerated end of the tendon.

For the embodiment of the present invention as shown in FIGS. 4A and 5, applicator 30 preferably includes handle 32 with head 34 formed on one end thereof. As best shown in FIG. 4A, elastomeric tube retainer 36 is preferably attached to and extends from one side of head 34. Enlarged opening 38 having a generally oval shaped cross section is preferably formed in and extends through head 34. A similar enlarged opening or channel 40 is preferably formed in and extends through elastomeric tube retainer 36. The dimensions and configuration of enlarged openings or channels 38 and 40 are selected to allow inserting the lacerated end of a tendon therethrough. For one application channels 38 and 40 may have a generally oval shaped configuration with dimensions of approximately ten millimeters by five millimeters.

The dimensions of head 34 and retainer 36 of applicator 30 are selected to allow an elastomeric tube such as elastomeric tube 20, 20a or 20b to be rolled up into the general configuration of oval shaped ring or toroid 28 and placed over the exterior of retainer 36 as best shown in FIG. 4A and 4B. Applicator 30 will preferably hold elastomeric tube 20, 20a or 20b in an expanded or stretched state so that the lacerated end of a tendon or ligament may be inserted through channels 38 and 40 and elastomeric tube 20, 20a or 20b disposed on the exterior of retainer 36.

For one application, retainer 36 has a generally oval shaped cross section with interior dimensions of approximately ten millimeters by five millimeters (10×5 mm), exterior dimensions of approximately eleven millimeters by six millimeters (11×6 mm) and extends a distance of approximately three millimeters (3 mm) from head 34. Portions of head 34 immediately adjacent to retainer 36 may also have a generally oval shaped configuration with exterior dimensions of approximately thirteen millimeters by eight millimeters (13×8 mm) and interior dimensions of approximately ten millimeters by five millimeters (10×5 mm). Head 34 may have a nominal thickness of approximately two millimeters (2 mm).

Handle 32, head 34 and retainer 36 may be formed as a single, integral unit using injection molding or other suitable manufacturing techniques. For other applications handle 32, head 34 and/or retainer 36 may be releasably secured with each other to allow attaching components with different dimensions to each other. For embodiments of the present invention such as shown in FIGS. 4A and 5, applicator 30 may be formed from two segments designated 30a and 30b which are joined with each other by hinge 42.

Segment 30a preferably includes respective handle portion 32a, head portion 34a and elastomeric tube retainer portion 36a. In a similar manner segment 30b preferably includes handle portion 32b, head portion 34b and elastomeric tube retainer portion 36b. Segments 30a and 30b are preferably formed as respective single integrated units using injection molding techniques and/or other manufacturing techniques as appropriate. For other applications, segments 30a and/or 30b may be formed from multiple components which are attached to each other using suitable mechanical fasteners (not expressly shown) and/or adhesive bonding (not expressly shown).

Figure 13:
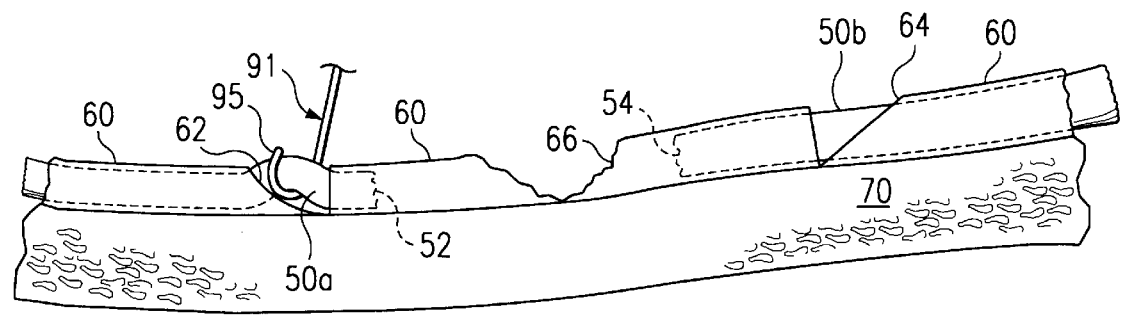
FIG. 13 is a schematic drawing in section and in elevation with portions broken away showing the lacerated sheath and tendon of FIG. 12 with proximal and distal incisions surgically formed in the sheath and one lacerated end of the tendon engaged with a hook.

For the embodiment of the present invention as best shown in FIG. 5, handle portion 32a preferably includes slot 46 disposed therein and extending from hinge 42. Handle portion 32b preferably includes rib or protrusion 48 extending longitudinally from hinge 42 and projecting toward slot 46. The dimensions and configuration of slot 46 and rib 48 are preferably selected such that rib 48 will snugly fit within slot 46 when applicator 30 is in its first, closed position as shown in FIGS. 4A and 13. Slot 46 and rib 48 cooperate with each other to stabilize handle 32 during placement of applicator 30 over the lacerated end of a tendon.

For the embodiment of the present invention as shown in FIGS. 4A, 4B and 5, when an elastomeric tube is rolled up and placed on retainer 36, handle portions 32a and 32b and head portions 34a and 34b are held in their first, closed position as shown in FIG. 4A and shown by dotted lines in FIG. 5. When the elastomeric tube has been unrolled from retainer 36 and placed over the lacerated end of a tendon, hinge 42 allows opening applicator 30 by moving handle segments 32a and 32b to their second open position as shown in FIG. 5. Handle portion 32a preferably includes projection 43 extending from hinge 42 to assist in opening applicator 30.

Figure 6:
FIG. 6 is a schematic drawing showing a side view of a suture/thread snare satisfactory for use with the present invention.

Suture thread snare 90 as shown in FIG. 6 includes semi-rigid rod 92 with open loop 94 extending from one end thereof. Rod 92 preferably has a diameter of approximately two millimeters (2 mm). Open loop 94 has an outside diameter of approximately three millimeters (3 mm) and an inside diameter of approximately two millimeters (2 mm) and a thickness of approximately two millimeters (2 mm). End 96 of open loop 96 is preferably spaced from rod 92 to form slot 98 there between. Suture thread snare 90 is preferably formed from flexible, disposable materials.

Figure 7:
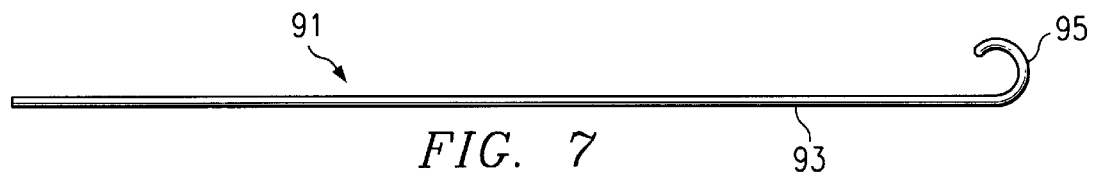
FIG. 7 is a schematic drawing showing a side view of a hook satisfactory for use with the present invention.

Various types of surgical instruments may be satisfactorily used to manipulate and/or position the lacerated end of a tendon, ligament or other types of fibrous body tissue to allow placing an elastomeric tube thereon in accordance with teachings of the present invention. Surgical hook 91, as shown in FIG. 7, represents one example of such surgical instruments. Surgical hook 91 preferably includes semirigid rod 93 with hook 95 extending from one end thereof. Rod 93 may be formed from similar materials and have generally corresponding dimensions as previously described rod 92. The dimensions, configuration and type of materials used to form suture thread snare 90 and surgical hook 91 are preferably selected to be compatible with the specific tendons, ligaments or other types of fibrous body tissue on which an elastomeric tube will be disposed in accordance with teachings of the present invention.

Figure 8:
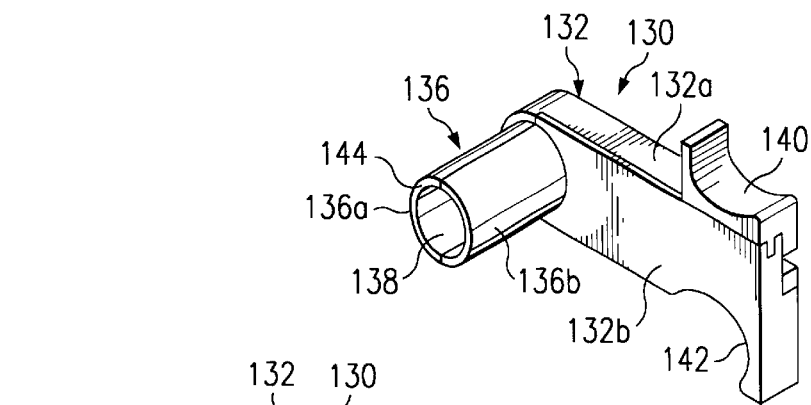
FIG. 8 is a schematic drawing showing an isometric view of an applicator incorporating a further embodiment of the present invention in its first, closed position.
Figure 9:
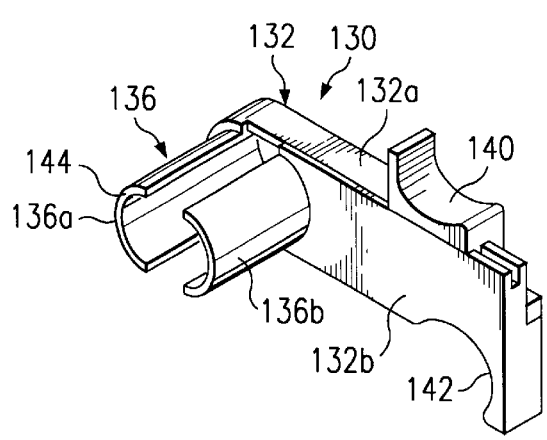
FIG. 9 is a schematic drawing showing an isometric view of the applicator of FIG. 8 in its second, open position.
Figure 16:
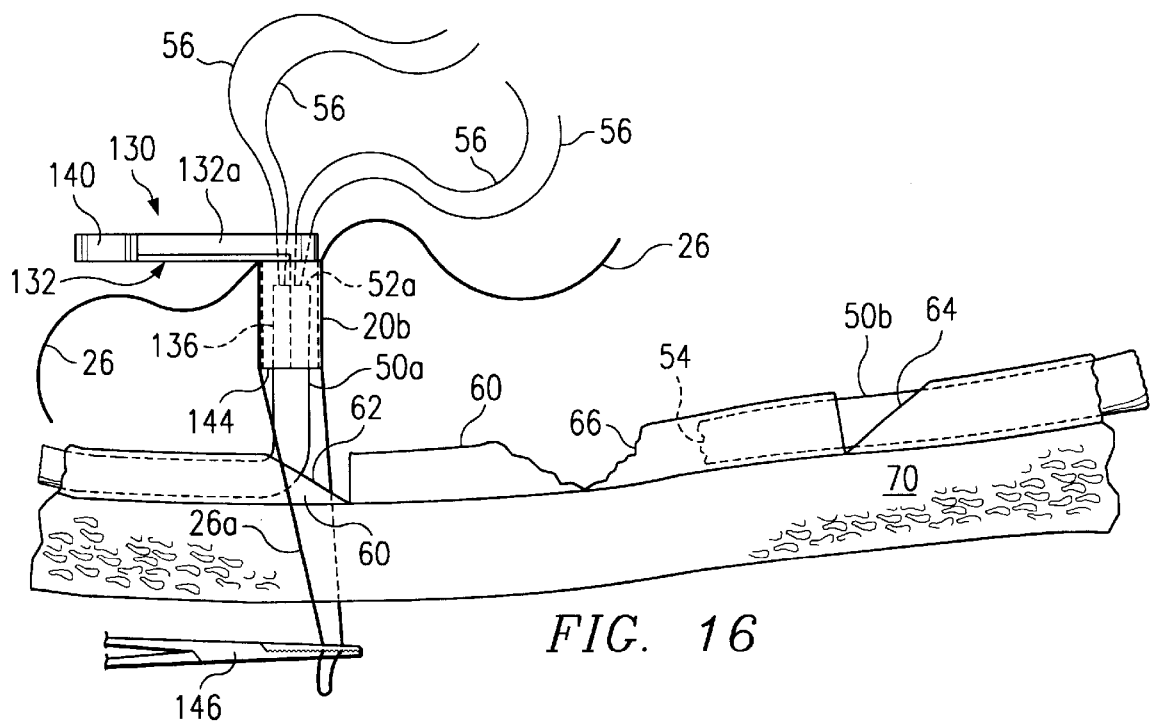
FIG. 16 is a schematic drawing in section and in elevation with portions broken away showing the lacerated end of the tendon of FIG. 15 extending through an applicator to place an elastomeric tube over the lacerated end of the tendon in accordance with teachings of the present invention.
Figure 17:
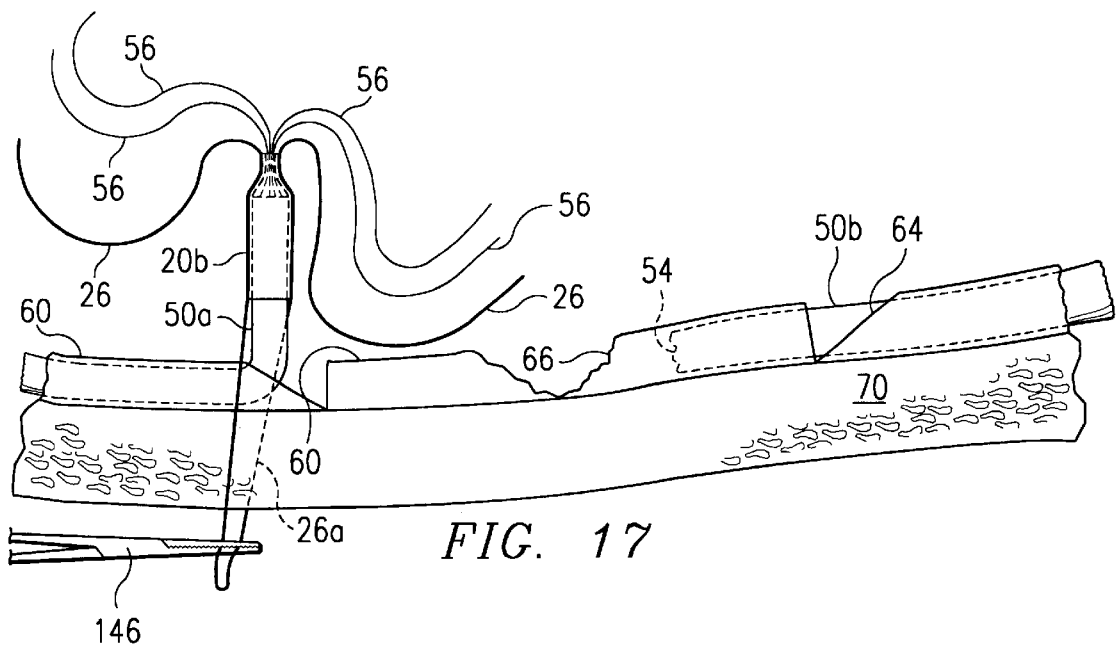
FIG. 17 is a schematic drawing in section and in elevation with portions broken away showing the elastomeric tube placed over the lacerated end of the tendon of FIG. 15 in accordance with teachings of the present invention.
Figure 18:
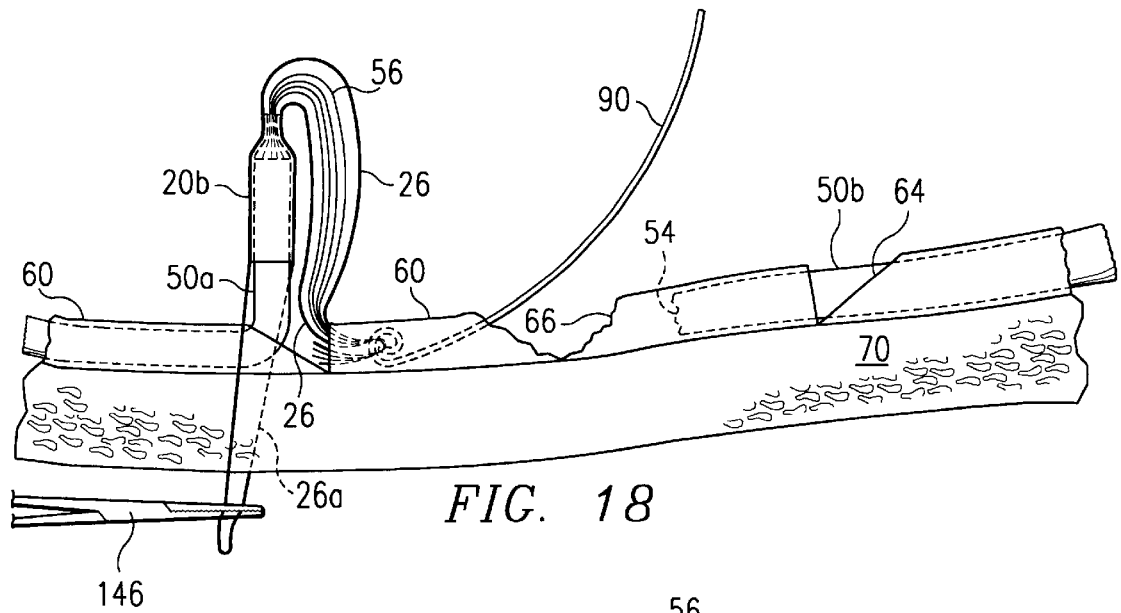
FIG. 18 is a schematic drawing in section and in elevation with portions broken away showing the suture thread snare of FIG. 6 engaged with sutures extending from the lacerated end of the tendon and threads extending from the elastomeric tube for use in reinserting the lacerated end of the tendon into the sheath in accordance with teachings of the present invention.
Figure 19:
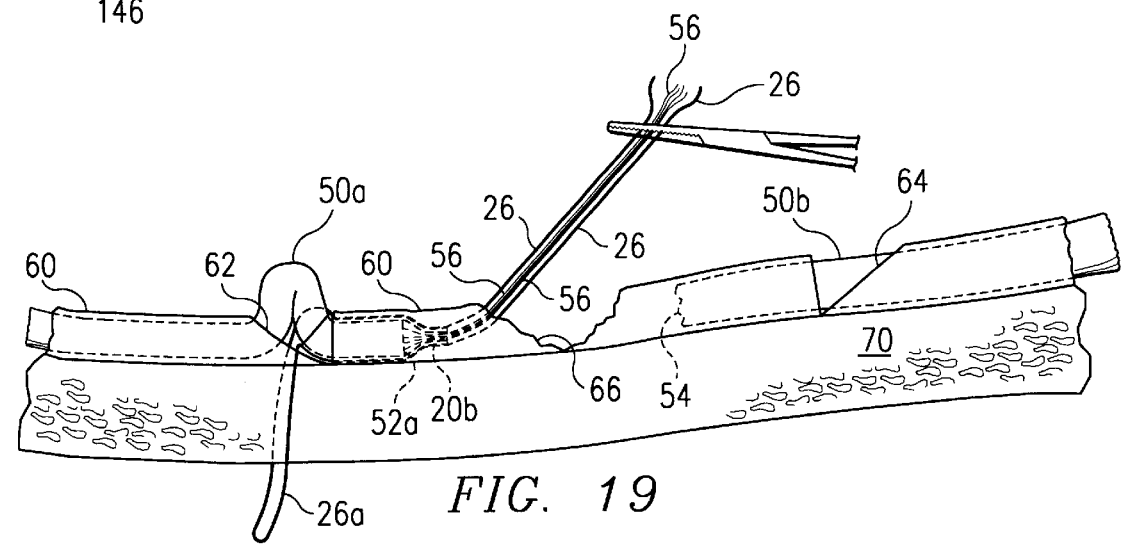
FIG. 19 is a schematic drawing in section and in elevation with portions broken away showing the lacerated end of the tendon and the elastomeric tube partially reinserted into the sheath in accordance with teachings of the present invention.
Figure 20:
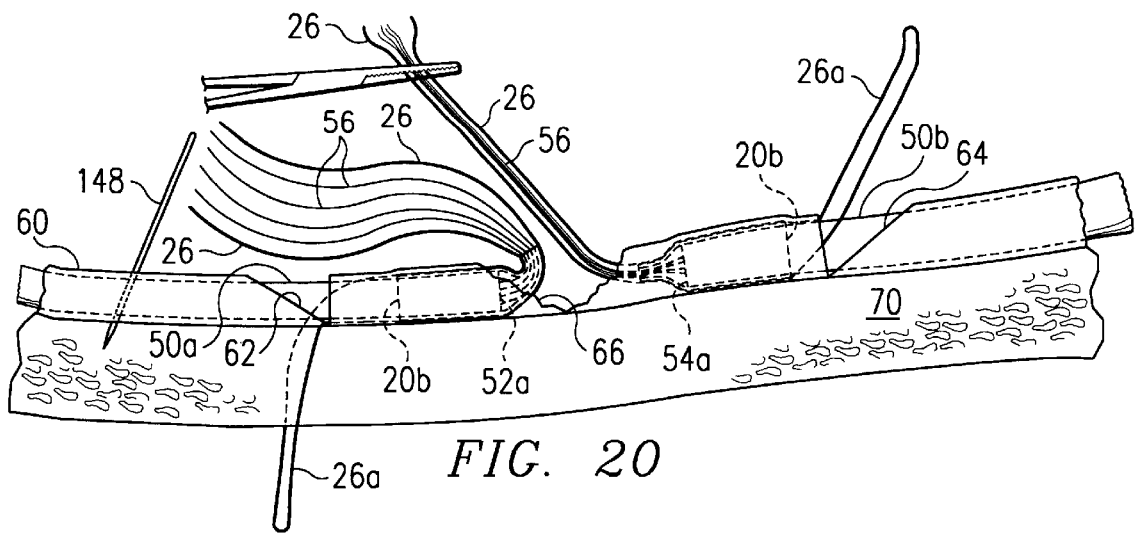
FIG. 20 is a schematic drawing in section and in elevation with portions broken away showing two elastomeric tubes respectively placed over lacerated ends of the tendon of FIG. 12 in accordance with teachings of the present invention.
Figure 21:
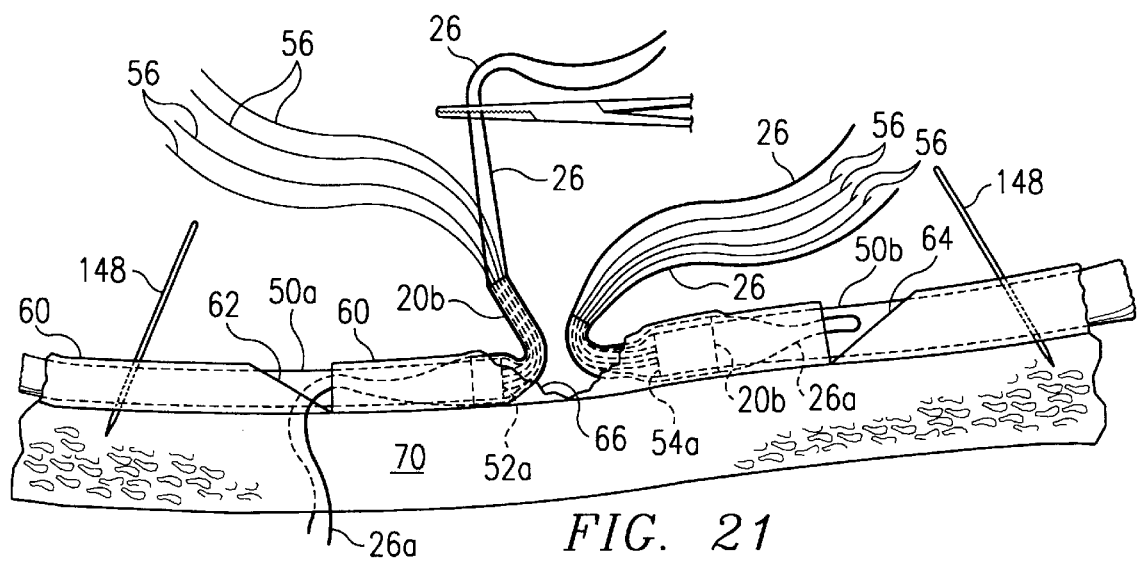
FIG. 21 is a schematic drawing in section and in elevation with portions broken away showing the elastomeric tubes and respective lacerated ends of the tendon of FIG. 20 with one elastomeric tube partially removed from its respective lacerated end.
Figure 22:
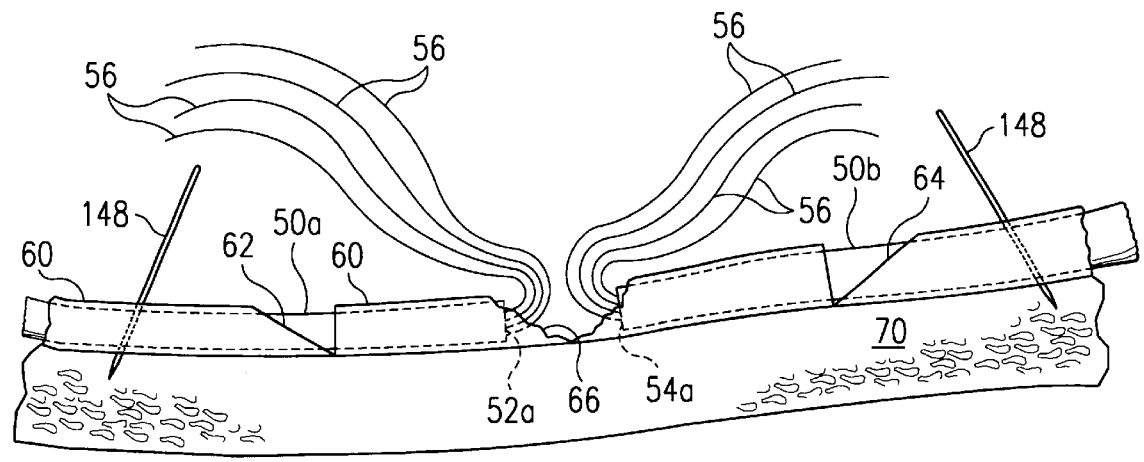
FIG. 22 is a schematic drawing in section and in elevation with portions broken away showing the lacerated ends of the tendon of FIG. 9 having respective suture strands extending from the lacerated ends disposed in opposition to each other in accordance with teachings of the present invention.
Figure 23:
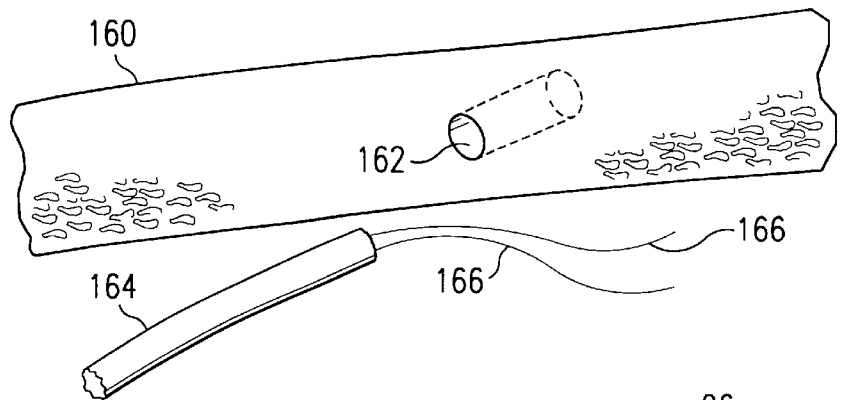
FIG. 23 is a schematic drawing in elevation with portions broken away showing a bone having a tunnel formed therein and one end of a tendon graft with suture strands disposed in and extending therefrom.
Figure 24:
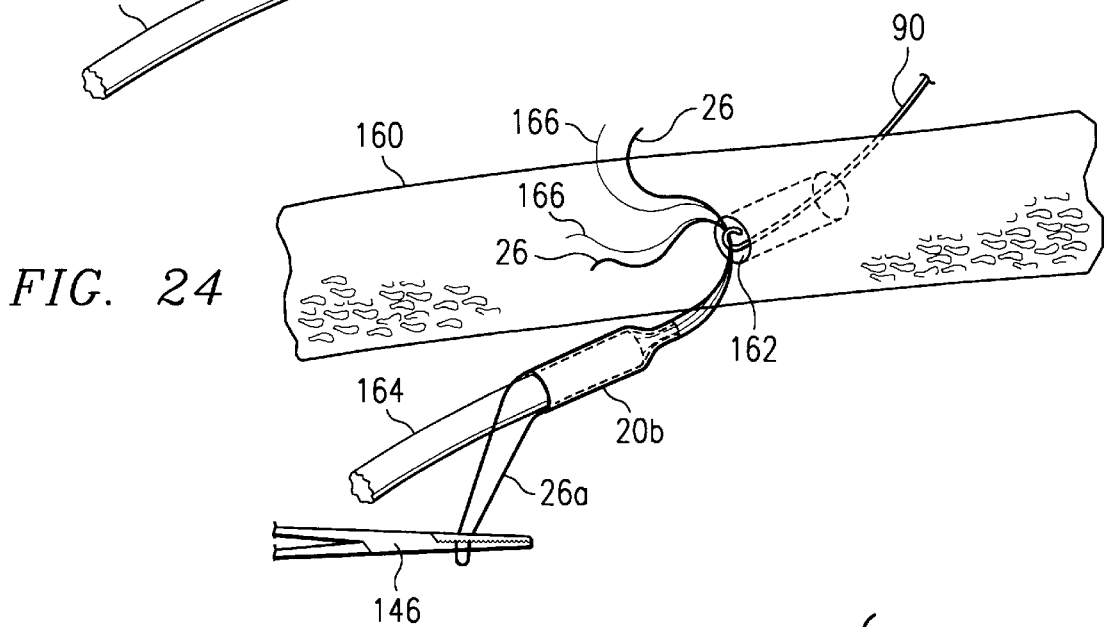
FIG. 24 is a schematic drawing in elevation with portions broken away showing the tendon graft of FIG. 23 with an elastomeric tube disposed thereon and a suture thread snare extending through the bone tunnel to position the tendon graft within the bone tunnel in accordance with teachings of this present invention.
Figure 25:
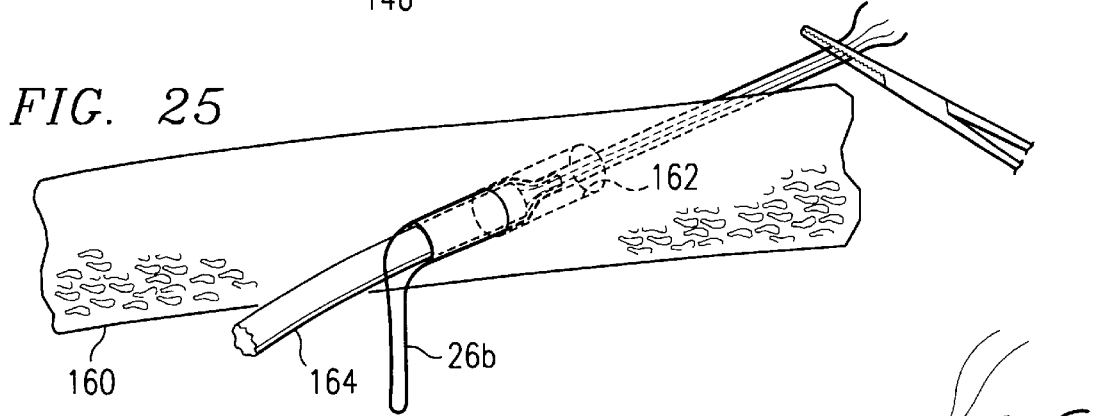
FIG. 25 is a schematic drawing in elevation with portions broken away showing the bone tunnel of FIG. 23 with the tendon graft partially disposed therein.
Figure 26:
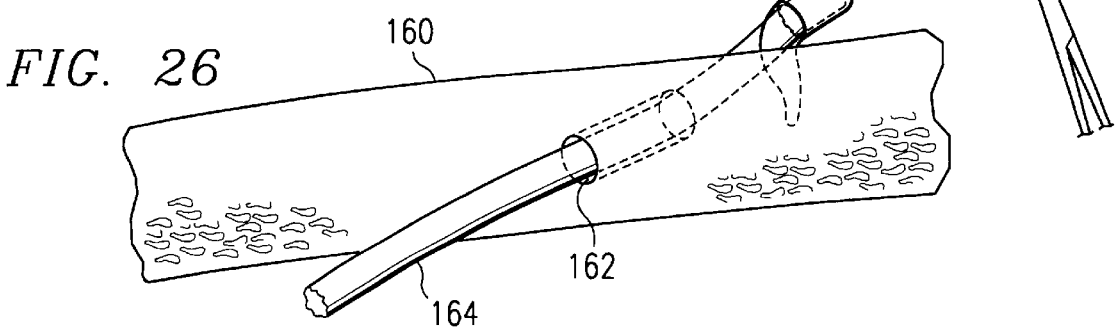
FIG. 26 is a schematic drawing in elevation with portions broken away showing the elastomeric tube partially removed from the end of the tendon graft in accordance with teachings of the present invention.

Applicator 130 incorporating an alternative embodiment of the present invention is shown in FIGS. 8, 9, and 16. For this particular embodiment, applicator 130 is preferably sized for relatively easy manipulation during a surgical procedure such as tenorrhaphy. Applicator 130 may be formed from various materials such as previously described with respect to applicator 30.

Applicator 130 may have an overall length of approximately four to five centimeters (4–5 cm). The dimensions and configuration of handle 132 are preferably selected to allow holding applicator 130 between a surgeon's index finger and thumb (not expressly shown). As discussed later in more detail, applicator 130 may be used to hold an elastomeric tube formed in accordance with teachings of the present invention in a stretched or expanded state so that applicator 130 with the elastomeric tube mounted thereon may be disposed over a lacerated end of a tendon at an appropriate location for sliding the elastomeric tube onto and over the lacerated end of the tendon.

For the embodiment of the present invention as shown in FIGS. 8, 9 and 16 applicator 130 preferably includes handle 132 with elastomeric tube retainer 136 formed on one end thereof and extending from one side thereof. Handle 132 preferably includes at least two components, 132a and 132b, which are slidably disposed relatively to each other. Elastomeric tube retainer 136 also preferably includes at least two components 136a and 136b which are attached to and extend from respective handle components 132a and 132b.

For the embodiment of the present invention as shown in FIGS. 8, 9 and 16, applicator 130 preferably has a first, closed position with retainer component 136a engaged with retainer component 136b to form opening 138 having a generally circular cross section. Opening 138 preferably extends through elastomeric tube retainer 136 and handle 132 to allow placing the lacerated end of a tendon, ligament or other types of fibrous body tissue therein. Opening 138 functions similar to previously described openings or channels 38 and 40 of applicator 30.

The interior dimensions of opening 138 are preferably selected to be compatible with the lacerated end of a tendon, ligament or other type of fibrous body tissue which will be disposed therein. The exterior dimensions of elastomeric tube retainer 136 are preferably selected to be compatible with an elastomeric tube which will be slidably disposed on the exterior thereof in accordance with teachings of the present invention.

Applicator 130 preferably has a second, open position such as shown in FIG. 9 which allows inserting the lacerated end of a tendon, ligament or fibrous body tissue therein. For the embodiment of the present invention as shown in FIGS. 8 and 9, handle component 132 preferably includes thumb rest 140 and handle component 132b preferably includes finger notch 142. Therefore, a surgeon may easily slide handle component 132a and 132b relative to each other to move applicator 130 between its first, closed position (FIG. 8) and its second, open position (FIG. 9). When applicator 130 is in its second position, retainer 136 will hold an elastomeric tube in an expanded or stretched state such that the lacerated end of a tendon or ligament may be inserted through opening 138 with an elastomeric tube disposed on the exterior of retainer 136.

Figure 10:
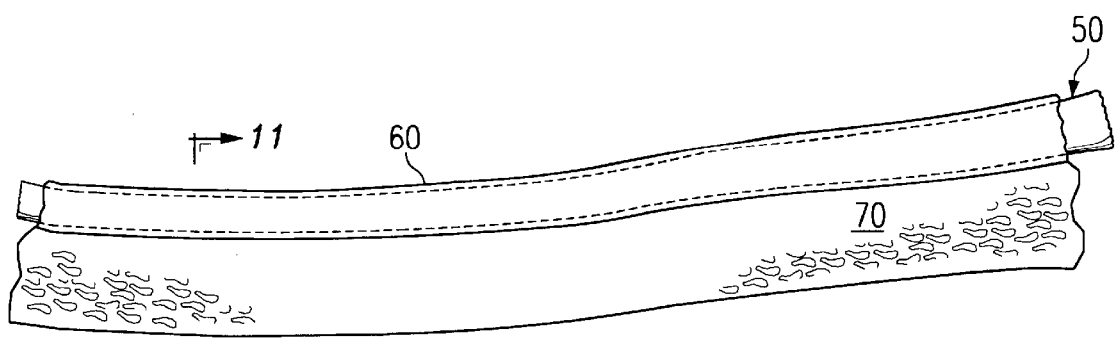
FIG. 10 is a schematic drawing in section and in elevation with portions broken away showing portions of a typical flexor tendon disposed within a sheath attached to a bone.
Figure 11:
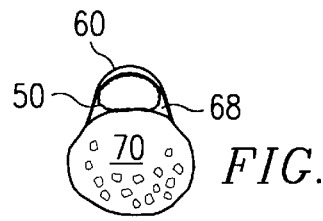
FIG. 11 is a schematic drawing in section taken along lines 11—11 of FIG. 10.

For purposes of illustrating teachings of the present invention, elastomeric tube 20b and applicator 130 will be described in more detail with respect to performing tenorrhaphy on lacerated flexor tendon 50. See FIGS. 10–22. FIGS. 10 and 11 are schematic representations of a typical flexor tendon 50 enclosed within osteofibrous sheath 60. Sheath 60 is attached to bone 70 which may represent a portion of patient's finger. Sheath 60 forms tunnel 68 with tendon 50 disposed therein. Sheath 60 protects tendon 50 and functions similar to a pulley mechanism to prevent bow stringing of tendon 50 during normal movement of the associated finger. The interior of sheath 60 is lined with a thin tenosynovium (not expressly shown) which produces synovial fluid (not expressly shown) to lubricate the interface between the exterior of tendon 50 and adjacent interior portions of sheath 60. The synovial fluid also provides nutrition for tendon 50.

Figure 12:
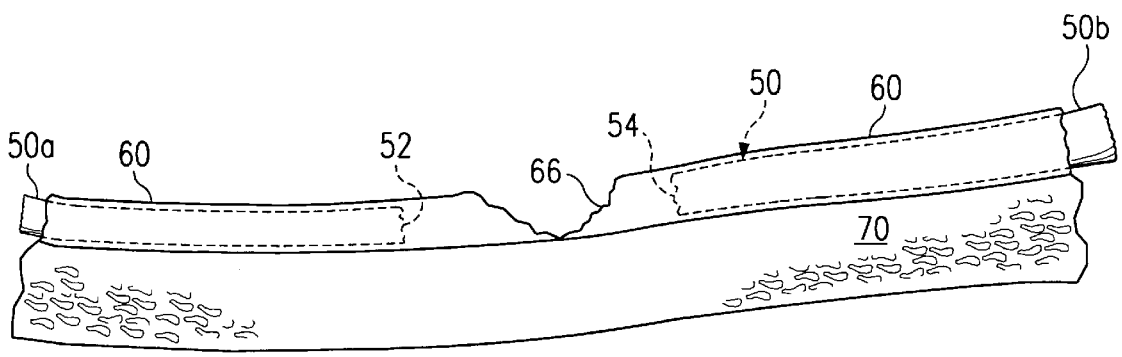
FIG. 12 is a schematic drawing in section and in elevation with portions broken away showing results often associated with lacerating the tendon and sheath of FIG. 10.

FIGS. 12 through 22 are schematic drawings which show one embodiment of the present invention and one type of surgical procedure which may be satisfactorily performed in accordance with teachings of the present invention. FIG. 12 shows typical results from lacerating tendon 50 and its associated sheath 60. For the example shown in FIG. 12, trauma to the associated finger may result in forming laceration site 66 in sheath 60. When tendon 50 is lacerated, lacerated ends 52 and 54 of respective tendon portions 50a and 50b will typically retract from each other and from laceration site 66.

Distal portion 50a of lacerated tendon 50 will often retract from laceration site 66 due to muscle forces. Proximal portion 50b of lacerated tendon 50 will often retract from laceration site 66 due to unopposed extension of the associated finger. As a result, lacerated ends 52 and 54 will often not be immediately available at laceration site 66 in sheath 60 for performing tendon repair.

Lacerated ends 52 and 54 of tendon 50 may retract sufficient distance from laceration site 66 such that surgical instruments, such as forceps and/or tendon retrievers (not expressly shown), cannot be satisfactorily used. Blind attempts with surgical instruments through laceration site 66 to retrieve lacerated ends 52 and 54 may cause additional serious damage to sheath 60 and/or tendon 50. Sheath 60 is relatively delicate and any additional injury or damage to sheath 60 may cause postoperative adhesions and substantially affect the success of the tendon repair.

Lacerated ends 52 and 54 of tendon 50 are generally ragged and uneven. As a result, lacerated ends 52 and 54 may catch on natural variations which are present in the interior of sheath 60 when attempts are made to pull ends 52 and 54 therethrough. Even if ends 52 and 54 may be satisfactorily grasped through laceration site 66, it may not be possible to deliver sufficient lengths of lacerated tendon 50 through laceration site 66 to accomplish the desired tendon repair.

Figure 14:
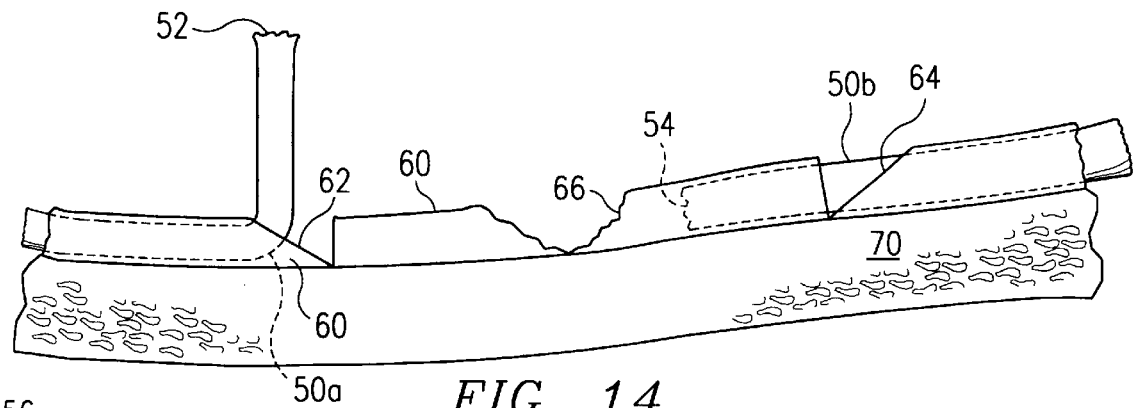
FIG. 14 is a schematic drawing in section and in elevation with portions broken way showing the lacerated sheath and tendon of FIG. 13 with the one lacerated end of the tendon extending from the distal incision.

As a result, one or more additional openings or incisions are often surgically created in sheath 60 adjacent to the laceration site 66 to provide access to respective lacerated ends 52 and 54 of tendon 50. For the embodiment of the present invention as shown in FIGS. 13 through 22, openings or incisions 62 and 64 may be surgically formed in sheath 60, distal and proximal to laceration site 66, using conventional surgical techniques. As shown in FIGS. 13 and 14, lacerated end 52 of tendon 50 may then be withdrawn through opening 62 using a standard surgical hook 91.

Figure 15:
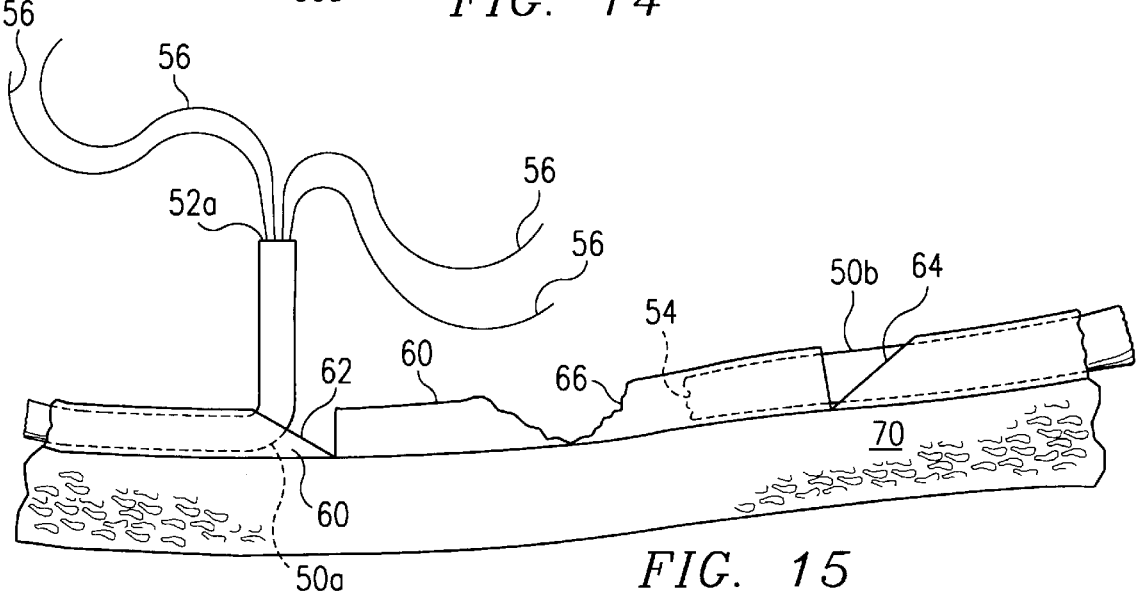
FIG. 15 is a schematic drawing in section and in elevation with portions broken away showing the one lacerated end of the tendon of FIG. 14 with a plurality of suture strands disposed in and extending therefrom.

A plurality of sutures 56 are preferably placed within and extend from lacerated end 52 of tendon 50 as shown in FIG. 15. Various techniques may be satisfactorily used for placing sutures 56 in lacerated end 52 of tendon 50. One example of placing sutures in the lacerated end of a tendon is shown in co-pending U.S. patent application Ser. No. 09/286,198 entitled Apparatus and Method for Placing Suture in the Lacerated End of a Tendon and Similar Body Tissues filed Apr. 5, 1999.

Often, lacerated end 52 will be trimmed to remove any oblique, jagged or crushed portions prior to placing suture strands 56 therein. As a result, a generally smooth, perpendicular surface 52a will be formed on the extreme end of tendon portion 50a. 52a is used to indicate this smooth, trimmed surface on the extreme end of tendon portion 50a in FIGS. 15–22.

Lacerated end 52 of tendon 50 with sutures 56 extending therefrom is preferably inserted through channel 138 in applicator 130 as shown in FIG. 16. An elastomeric tube such as elastomeric 20b is preferably mounted on retainer 136. Handle 132 may be used to position applicator 130 and elastomeric tube 20b at the desired position relative to lacerated end 52a of tendon 50. For some applications, end 144 of retainer 136 of applicator 130 will be positioned between approximately one-half centimeter and one centimeter from lacerated end 52a of tendon 50 as shown in FIG. 16. When applicator 130 is in the desired position relative to end 52a, threads 26 may be used to slide elastomeric tube 20b from retainer 136 to cover the exterior surface of tendon portion 50a adjacent to lacerated end 52a.

For some applications a patient's finger may be extended through loop 26a prior to inserting lacerated end 52 of tendon portion 50a within opening 138. FIGS. 16–20. For other applications, loop 26a may be positioned adjacent to the patient's finger or other bone. See FIGS. 23–26. For purposes of explanation bone 70 is shown disposed within loop 26a in FIGS. 16–20. However, loop 26a may be satisfactorily used in other locations or orientations. See FIGS. 23–26. When a patient's finger or bone is placed within loop 26a, loop 26a must generally be cut prior to removing the associated elastomeric loop from the respective lacerated end of a tendon, ligament or other type of fibrous body tissue. See FIG. 21.

Forceps 146 or another suitable surgical instrument are preferably engaged with loop 26a to assist with sliding applicator 130 and elastomeric tube retainer 136 relative to elastomeric tube 20b and at the same time maintaining the desired position of elastomeric tube 20b relative to lacerated end 52a. Typically, applicator 130 will be placed in its second, open position prior to inserting tendon portion 50a therein. Applicator 130 will generally remain in its second, open position for placement of elastomeric tube 20b on lacerated end 52a. For small tendons or ligaments, handle 132 may be used to move applicator 130 to its first, closed position.

Elastomeric tube 20b is preferably slid onto and over lacerated end 52a of tendon portion 50a. First end 21 of elastomeric tube 20b will preferably extend beyond lacerated end 52a of tendon portion 50a. One of the technical benefits of the present invention is protection of lacerated end 52a by extending elastomeric tube 20b thereover.

Suture thread snare 90 may be used to pass threads 26 extending from first end 21 of elastomeric tube 20b and sutures 56 extending from lacerated end 52a of tendon portion 50a through sheath 60 to laceration site 66. See FIG. 18. Forceps 146 and loop 26a cooperate with suture thread snare 90 to maintain elastomeric tube 20b at this desired location on tendon portion 50a.

Elastomeric tube 20b will contract and compress lacerated end 52a of tendon portion 50a to prevent fraying. Elastomeric tube 20b will also prevent lacerated end 52a from catching on opening 62 or contacting the interior of sheath 60. Materials used to form elastomeric tube 20b and its associated dimensions are preferably selected so that when end 52a of lacerated tendon 50 is compressed within longitudinal passageway 24 of elastomeric tube 20b, the combined exterior dimensions of elastomeric tube 20b with end 52a disposed therein will be less than the interior dimensions of tunnel 68 extending through sheath 60.

Sutures 56 and threads 26 may be used to pull first end 21 of elastomeric tube 20b and lacerated end 52a of tendon portion 50a into opening 62 and through the sheath 60 to laceration site 66. By simultaneously pulling both sutures 56 and threads 26 with suture thread snare 90 or another suitable instrument, tendon portion 50a may be manipulated as desired without displacing elastomeric tube 20b from lacerated end 52a.

Similar surgical procedures may be used to form opening 64 and attach a second elastomeric tube 20b to lacerated end 54a of tendon portion 50b. When lacerated ends 52a and 54a are available at laceration site 66, needles 148 or other appropriate surgical devices (not expressly shown) may be used to temporarily transfix lacerated ends 52a and 54a at the desired location within sheath 60. For some applications, needles 148 may be inserted through sheath 60 and tendon portions 50a and 50b to temporarily maintain the desired alignment and spacing between lacerated ends 52a and 54a. See FIGS. 20, 21 and 22.

Threads 26 may be used to remove elastomeric tubes 20b from respective lacerated ends 52a and 54a by releasing respective loops 26a and pulling threads 26 to slide respective elastomeric tubes 20b off of tendon portions 50a and 50b. Sutures 56 may then be used to attach lacerated ends 52a and 54a with each other. After lacerated ends 52a and 54a are attached, the needles 148 used to temporarily maintain the alignment of lacerated ends 52a and 54a may be removed.

If either lacerated end 52 or 54 of tendon 50 is available at laceration site 66, it may only be necessary to form one additional opening in sheath 60 and to install only one elastomeric tube 20b on the retracted lacerated end 52 or 54. For some applications, laceration site 66 may not be the appropriate location for conducting the tendon repair. One of the technical benefits of the present invention includes the ability to position lacerated ends 52a and 54a at the optimum location within the associated sheath 60 to carry out the desired tendon repair procedure.

Elastomeric tubes, applicators and suture thread snares with other configurations and dimensions may be manufactured in accordance with teachings of the present invention to accommodate other types of body tissues and/or other surgical procedures, such as the passing of grafts through bone tunnels. The grafts may include artificial and/or natural tissue. During joint reconstructive surgery, a graft is commonly passed through a bone tunnel such as in anterior cruciate ligament reconstruction where the graft is passed through a bone tunnel formed in the tibia. Another example of passing a graft through a bone tunnel is joint reconstructive surgery for arthritis such as arthroplasty of the carpometacarpal joint of the thumb where the graft is commonly passed through a bone tunnel in the metacarpal. Apparatus and method incorporating teachings of the present invention may be provided to aid in such surgical procedures.

FIGS. 23–26 show one example of passing a tendon graft through a tunnel in a bone in accordance with teachings of the present invention. Bone 160, shown with tunnel or hole 162 formed therein, is intended to be representative of any bone in a patient's body. The diameter of tunnel 162 is preferably selected to be slightly larger than the diameter of tendon graft 164 which will be disposed therein. Tendon graft 164 preferably includes a pair of suture threads 166 extending therefrom. In accordance with teachings of the present invention, elastomeric tube 20b is installed on the end of tendon graft 164. Suture thread snare 90 may be inserted through tunnel 162 and engaged with sutures 166 and threads 26. Although typically not required, for some applications, forceps 146 may be engaged with loop 26a to assist with maintaining elastomeric tube 20b at the desired location on tendon graft 164. Elastomeric tube 20b in cooperation with suture threads 26 engaged by snare 90 may be used to guide tendon graft 164 through bone tunnel 162 using similar techniques as previously described with respect to tendon portion 50a and sheath 60.

Although the present invention has been described in detail, it should be understood that various changes, substitutions and alterations can be made hereto without departing from the spirit and scope of the invention as defined by the appended claims.

We claim:

1. An elastomeric tube for covering a lacerated end of a tendon comprising:

the elastomeric tube formed from flexible, resilient material having sufficient elasticity to allow portions of the elastomeric tube defined by a generally oval shaped cross section with at rest dimensions of two to four millimeters to expand to approximately twelve to fourteen millimeters;

a first end and a second end with a longitudinal passageway extending therethrough;

the longitudinal passageway having the generally oval shaped cross section operable to expand to receive the lacerated end of the tendon therein;

a plurality of threads engaged with the elastomeric tube; and the threads extending longitudinally from at least the first end of the elastomeric tube.

2. The elastomeric tube of claim 1 further comprising a loop formed by the threads extending from the second end of the elastomeric tube.

3. An elastomeric tube for covering a lacerated end of a tendon comprising:

the elastomeric tube formed from flexible, resilient material having sufficient elasticity to allow portions of the elastomeric tube defined by a diameter with at rest dimensions of two to four millimeters to be expanded to approximately twelve to fourteen millimeters;

a first end and a second end with a respective opening formed at each end and a longitudinal passageway extending therethrough;

the longitudinal passageway having the generally circular shaped cross section operable to expand to receive the lacerated end of the tendon therein;

a plurality of threads engaged with the elastomeric tube; and the threads extending longitudinally from at least the first end of the elastomeric tube.

4. The elastomeric tube of claim 3 further comprising a loop formed by the threads extending from the second end of the elastomeric tube.

* * * * *